United States Patent [19]

Santel et al.

[11] Patent Number: 5,593,942
[45] Date of Patent: Jan. 14, 1997

[54] HERBICIDAL AGENTS BASED ON HETEROARYLOXYACETAMIDES AND METRIBUZIN

[75] Inventors: Hans-Joachim Santel, Leverkusen; Dieter Feucht, Monheim, both of Germany

[73] Assignee: Bayer Aktiengesellschaft, Leverkusen, Germany

[21] Appl. No.: 356,401

[22] PCT Filed: Jul. 5, 1993

[86] PCT No.: PCT/EP93/01732

§ 371 Date: Dec. 28, 1994

§ 102(e) Date: Dec. 28, 1994

[87] PCT Pub. No.: WO94/02014

PCT Pub. Date: Feb. 3, 1994

[30] Foreign Application Priority Data

Jul. 16, 1992 [DE] Germany .................. 42 23 465.4

[51] Int. Cl.$^6$ .................. A01N 43/707; A01N 43/824
[52] U.S. Cl. .................................................. 504/134
[58] Field of Search ........................................... 504/134

[56] References Cited

U.S. PATENT DOCUMENTS

| | | | |
|---|---|---|---|
| 4,256,482 | 3/1981 | Wittmann et al. | 71/92 |
| 4,530,717 | 7/1985 | Aya et al. | 71/90 |
| 4,717,415 | 1/1988 | Ditgens et al. | 71/93 |
| 4,840,663 | 6/1989 | Quandranti et al. | 71/93 |
| 4,929,743 | 5/1990 | Förster et al. | 548/187 |
| 4,968,342 | 11/1990 | Förster et al. | 71/90 |
| 5,090,991 | 2/1992 | Förster et al. | 71/90 |

FOREIGN PATENT DOCUMENTS

| | | |
|---|---|---|
| 1202499 | 1/1986 | Canada . |
| 0009616 | 8/1978 | European Pat. Off. . |
| 0067713 | 6/1982 | European Pat. Off. . |
| 0108237 | 5/1984 | European Pat. Off. . |
| 0155493 | 2/1985 | European Pat. Off. . |
| 0195237 | 11/1986 | European Pat. Off. . |
| 0257771 | 3/1988 | European Pat. Off. . |
| 0290257 | 11/1988 | European Pat. Off. . |
| 0348737 | 6/1989 | European Pat. Off. . |
| 0427695 | 10/1990 | European Pat. Off. . |
| 0537543 | 4/1993 | European Pat. Off. . |
| 2950682 | 12/1978 | Germany . |
| 3238007 | 4/1984 | Germany . |
| 3434982 | 4/1986 | Germany . |
| 3600997 | 7/1987 | Germany . |
| 559507 | 3/1975 | Switzerland . |
| 2042339 | 9/1978 | United Kingdom . |

OTHER PUBLICATIONS

Research Disclosure (Jan. 1981) N. 201, Havant, Hamshire, England pp. 9–17.
Certified Translation of OEP 34 06 655.1 pp. 1–12. Feb. 1985.
Chemical Abstract vol. 104, (1986) p. 236 104:220815a.

*Primary Examiner*—S. Mark Clardy
*Attorney, Agent, or Firm*—Sprung Horn Kramer & Woods

[57] ABSTRACT

The novel herbicidal active ingredient combinations consisting of (1) a heteroaryloxyacetamide of the general formula (I)

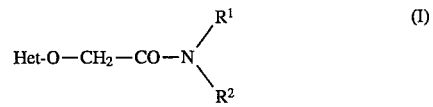

in which Het, $R^1$ and $R^2$ have the meanings given in the description (=active ingredients of group 1) and (2) a known herbicidal active ingredient from group 2, which comprises the substance classes consisting of the phenyl- and benzothiazolylureas, dinitroanilines, triazines, triazinones, sulphonylureas, imidazolinones, pyridinecarboxamides and diphenyl ethers, exhibit synergistie effects in certain weight ratios and can be used as selective herbicides in various crop plants (for example wheat, barley and maize).

Synergistic active ingredient combinations of N-iso-propyl-N-(4-fluorophenyl)-(5-trifluoromethyl -1,3,4-thiadiazol-2-yl-oxy)-acetamide and isoproturon, methabenzthiazuron or metribuzine may be mentioned as examples.

10 Claims, No Drawings

HERBICIDAL AGENTS BASED ON HETEROARYLOXYACETAMIDES AND METRIBUZIN

This application has been filed under 35 USC 371 from international application PCT/EP93/01732, filed Jul. 5, 1993 and published as WO94/02014 Feb. 3, 1994.

The invention relates to novel herbicidal, synergistic combinations of the known heteroaryloxyacetamides on the one hand and further known herbicides belonging to other classes of substances on the other hand, which can be particularly advantageously used for selectively combatting weeds in various crops/plants.

The patent specifications cited below describe heteroaryloxyacetamides which are preferentially effective against monocotyledon weeds (=grass weeds) but also against some dicotyledon weeds. They exhibit practically exclusively soil activity and only slight activity via the foliage, and some of them have a high selectivity in mono- and dicotyledon crop plants, such as cereals, maize, rice, soya bean and cotton [cf. for example EP-A 5 501 (=U.S. Pat. No. 4,509,971 and U.S. Pat. No. 4,833,243); EP-A 18 497 (=U.S. Pat. No. 4,645,525 and U.S. Pat. No. 4,756,741); EP-A 29 171 (=U.S. Pat. No. 4,408,055); EP-A 94 514 (=U.S. Pat. No. 4,585,471); EP-A 100 044 (=U.S. Pat. No. 4,549,899); EP-A 100 045 (=U.S. Pat. No. 4,540,430); EP-A 161 602 (=U.S. Pat. No. 4,784,682); EP-A 195 237 (=U.S. Pat. No. 4,788,291); DE-A 3 724 467; EP-A 348 734 (=U.S. Pat. No. 4,988,380); EP-A 348 737 (=U.S. Pat. Nos. 4,968,342 and 5,090,991); DE-A 4 113 421 and DE-A 4 137 827, as well as WO 91/06544].

Surprisingly, biological experimentation has now uncovered a number of known herbicidally active compounds from the classes of the phenyl- and benzthiazolyl-ureas, imidazolinones, pyridinecarboxamides and diphenyl ethers which, when used together with the abovementioned heteroaryloxyacetamides, possess extremely synergistic properties with regard to the effectiveness against weeds and can be used particularly advantageously, that is to say as broadly effective combination preparations, for selectively combatting weeds—both monocotyledon and dicotyledon weeds, by the preemergence and postemergence methods—in monocotyledon and dicotyledon crop plants, such as, for example, maize, wheat, barley, rice, soya bean, cotton, beet and peanuts, so that a number of economically important (problem) weeds and grass weeds can be reliably controlled.

The present invention provides herbicidal synergistic agents, characterised by an effective content of an active ingredient combination consisting of (1) a heteroaryloxyacetamide of the general formula (I)

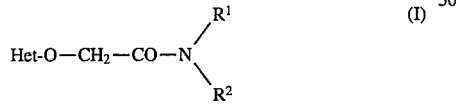

in which

Het represents an optionally substituted heteroaromatic radical from the series consisting of 1,3-thiazol-2-yl, 1,2,4-thiadiazol-2-yl, 1,3,4-thiadiazol-2-yl, benzoxazol-2-yl and benzothiazol-2yl.

$R^1$ represents $C_1$–$C_4$-alkyl, $C_3$–$C_4$-alkenyl or $C_1$–$C_4$-alkoxy, each of which is optionally substituted, and $R^2$ represents $C_1$–$C_4$-alkyl, $C_3$–$C_4$-alkenyl or phenyl, each of which is optionally substituted, (=active ingredients of group 1) and (2) a known herbicidal active ingredient from the group 2 which contains the compound classes (a) to (i) mentioned below:

(a) N-phenylureas, such as, for example, 3-(4-isopropylphenyl)-1,1-dimethylurea (ISOPROTURON), 3-(3-chloro-4-methylphenyl)-1,1-dimethylurea (CHLORTOLURON), 3-(3,4-dichlorophenyl) -1,1-dimethylurea(DIURON),3-(4-chlorophenyl) -1,1-dimethylurea (MONURON), 3-(3,4-dichlorophenyl) -1-methoxy-1-methylurea (LINURON), 3-(4-chlorophenyl)-1-methoxy-1-methyl-urea (MONOLINURON) or 3-(3-trifluoromethyl-phenyl) -1,1-dimethylurea (FLUOMETURON);

(b) N-benzthiazolyl-ureas, such as, for example, 3-(benzthiazol-2-yl)-1,3-dimethyl-urea (METHABENZTHIAZURON);

(c) 2,6-dinitroanilines, such as, for example, N,N-di-(n-propyl)-2,6-dinitro-4-trifluoromethylaniline (TRIFLURALIN) or N-(1-ethylpropyl)-3,4-dimethyl-2,6-dinitroaniline (PENDIMETHALIN);

(d) s-triazines, such as, for example, 2-chloro-4-ethylamino-6-isopropylamino-s-triazine (ATRAZINE), 2-chloro-4-(1-cyano-1-methylethyl-amino)-6-ethylamino-s-triazine (CYANAZINE). 2-Chloro-4-ethylamino-6-tert.butylamino-s -triazine (TERBUTHYLAZINE), 2-ethylamino-4-methylthio -6-tert.butylamino-s-triazine (TERBUTRYN) or2-chloro-4,6-bis-(ethylamino)-s-triazine (SIMAZINE);

(e) as-triazinones, such as, for example, 4-amino-6-tert.-butyl-3-methylthio-1,2,4-triazin -5-(4H)-one (METRIBUZINE), 3-methyl-4-amino-6-phenyl-1,2,4-triazin-5-(4H)-one (METAMITRON) or 4-amino-6-tert.-butyl-3-ethylthio-1,2,4-triaxin -5(4H)-one (ETHIOZINE);

(f) sulphonylureas, such as, for example, 3-(4-methoxy-6-methyl-1,3,5-triazin-2-yl)-1-(2-chlorophenyl)-sulphonylurea (CHLOROSULFURON), 3-(4-methoxy-6-methyl-1,3,5-triazin-2-yl)-1-(2-methoxycarbonyl-phenyl)-sulphonylurea (METSULFURON); 3-(4-methoxy-6-methyl-1,3,5-triazin-2-yl)-1-(2-methoxycarbonyl-thien-3-yl-sulphonylurea) (THIFENSULFURON), 3-(4-methoxy-6-methyl-1,3,5-triazin-2-yl)-3-methyl-1-(2-(methoxycarbonyl-phenyl)-sulphonylurea (TRIBENURON); 3-(4,6-dimethoxy-pyrimidin-2-yl)-1-(2-methoxycarbonyl-benzyl)-sulphonylurea (BENSULFURON), 3-(4-chloro-6-methoxypyrimidin-2-yl)-1-(2-ethoxycarbonyl-phenyl)-sulphonylurea (CHLORIMURON), 3-(4,6-dimethoxypyrimidin-2-yl)-1-(3-dimethylaminopyridin-2-yl)-sulphonylurea (NICOSULFURON), 3-(4-methoxy-6-methyl-1,3,5-triazin-2-yl)-1-[2-(2-chloroethoxy)-phenyl]-sulphonylurea (TRIASULFURON), 3-[4,6-bis-(difluoromethoxy)-pyrimidin-2-yl]-1-(2-methoxy-carbonylphenyl)-sulphonylurea (PRIMISULFURON) or 3-(4,6-dimethoxy-pyrimidin-2-yl)-1-(N-methyl-N-methylsulphonyl-amino)-sulphonylurea (AMIDOSULFURON);

(g) imidazolinones, such as, for example, 2-[4,5-dihydro-4-methyl-4-(1-methylethyl)-5-oxo-1H-imidazol-2-yl]-3-quinolinecarboxylic acid (IMAZAQUIN), 2-[4,5-dihydro-4-methyl-4-(1-methylethyl)-5-oxo-1H-imidazol-2-yl]-3-pyridinecarboxylic acid (IMAZAPYR) or methyl 2-[4,5-dihydro-4-methyl-4-(1-methylethyl)-5-oxo-1H-imidazol-2-yl]-methyl-benzoate (IMAZAMETHABENZ);

(h) pyridinecarboxamides, such as, for example, N-(2, 4-difluorophenyl)-2-(3-trifluoromethyl -phenoxy)-3-pyridinecarboxamide (DIFLUFENICAN); and (i) diphenyl ethers, such as, for example, 2,4-dichlorophenyl 3'-methoxycarbonyl-4'-nitrophenyl ether (BIFENOX), 5-(2-chloro-4-tri-fluoromethyl-phenoxy)-2-nitro-benzoic acid (ACIFLUORFEN), [1-(ethoxycarbonyl)-ethyl] 5-[2'-chloro-4'-trifluoromethyl-phenoxy]-2-nitro benzoate (LACTOFEN) or 5-(2-chloro-4-trifluoro-methyl-phenoxy)-N-methylsulphonyl-2-nitro-benzamide (FOMESAFEN);

(=active ingredients of group 2), in general 0.001 to 1,000 parts by weight of active ingredient of group (2) being used per 1 part by weight of active ingredient of group (1) (that is to say of the formula (I)).

Of particular interest are herbicidal agents according to the invention containing compounds of the stated formula (I) in which Het represents an optionally substituted 1,3,4-thia-diazol-2-yl radical, $R^1$ represents $C_1-C_4$-alkyl and $R^2$ represents optionally substituted phenyl, in combination with an N-phenylurea, an N-benzothiazolylurea or an as-triazinone.

Very particularly preferred herbicidal agents according to the invention contain, as a compound of the formula (I), N-isopropyl-N-(4-fluorophenyl)-5-trifluoromethyl-1,3,4-thiadiazol-2-yl-oxy)-acetamide of the formula (I-1)

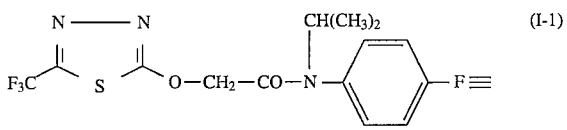

in combination with

| ISOPROTURON | = (IPU), |
| METHABENZTHIAZURON | = (MBT) or |
| METRIBUZINE | = (MBZ). |

The compound of the formula (I-1) is known, for example from EP-A 348 737 and U.S. Pat. No. 4,968,342. The other active ingredients of the general formula (I) are described in the patent specifications or applications cited at the outset.

The active ingredients of group (2) are described in "The Pesticide Manual", British Crop Protection Council, 8th Edition (1987): for example pages 491 to 492 (ISOPROTURON), page 538 (METHABENZTHIAZURON) and pages 573 to 574 (METRIBUZINE).

The heteroaryloxyacetamides of the formula (I) which are defined under group (1) act preferentially against monocotyledon weeds (=grass weeds) but additionally act against some dicotyledon weeds.

The active ingredients mentioned under group (2) can be used for selectively combatting a broad spectrum of weeds and grass weeds in economically important cultures, such as, for example, cereals, maize, soya bean, cotton, beet and rice. However, their action against certain monocotyledon and dicotyledon weeds is not always adequate. Important problem weeds, such as, for example, *Galium aparine* or Lolium species, are frequently only insufficiently combatted.

It has now been found, surprisingly, that the active ingredient combinations defined above and consisting of the heteroaryloxyacetamides of the formula (I) or group (1) and the active ingredients mentioned under group (2) have a particularly high activity and can be selectively used in many cultures.

Surprisingly, the herbicidal activity of the active ingredient combination according to the invention is substantially higher than the sum of the actions of the individual active ingredients.

There is thus an unforeseeable genuine synergistic effect present and not just an additive effect. The novel active ingredient combinations are well tolerated in many cultures, the novel active ingredient combinations also readily combatting weeds which are otherwise difficult to combat, such as *Galium aparine* and Lolium species. The novel active ingredient combinations thus represent a valuable enrichment of the selective herbicides.

The active ingredient combinations according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinocholoa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopercuru and Apera.

Monocotyledon weeds of the genera: Oryza, Zea, Triticum, Hordeum, Arena, Secale, Sorghum, Panicum, Saccharum, Ananas, Asparagus and Allium.

However, the use of the active ingredient combinations according to the invention is in no way restricted to these genera, but also extends in the same manner to other plants.

The synergistic effect of the active ingredient combination according to the invention is particularly pronounced at certain concentrations. However, the weight ratios of the active ingredients and the active ingredient combinations can be varied within relatively wide ranges. In general, 0.001 to 1,000 parts by weight, preferably 0.01 to 100 parts by weight, particularly preferably 0.1 to 30 parts by weight of active ingredient of group (2) are used per 1 part by weight of active ingredient of group (1) formula (I).

The active ingredients or active ingredient combinations can be converted into the customary formulations, such as solutions, emulsions, wettable powders, suspensions, powders, dusting agents, pastes, soluble powders, granules, suspension-emulsion concentrates, natural and synthetic materials impregnated with active ingredient, and very fine capsules in polymeric substance.

These formulations are produced in a known manner, for example by mixing the active ingredients with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methyl chloride, aliphatic carbons, such as cyclohexane or paraffins, for example petroleum fractions, mineral and vegetable oils, alcohols, such as butanol or glycol, as well as their ethers and esters, ketones, such as acetone, methyl ethyl ketone, methyl isobutyl ketone and cyclohexanone, strongly polar solvents, such as dimethylformamide and dimethyl sulphoxide, as well as water.

As solid carriers there are suitable: for example, ammonium salts and ground natural minerals, as kaolins, clays, talc, chalk, quartz, attapulgite, montmorillonite or diatomaceous earth, and ground synthetic minerals, such as finely divided silica, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example, nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as albumen hydrolysis products; as dispersing agents there are suitable: for example, lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further possible additives are mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations contain in general between 0.1 and 95% by weight of active ingredient combination, preferably between 0.5 and 90%.

The active ingredient combinations according to the invention are used in general in the form of finished formulations. However, the active ingredients contained in the active ingredient combinations can also be mixed in the form of individual formulations during use, that is to say they can be used in the form of tank mixes.

The novel active ingredient combinations, as such or in the form of their formulations, can furthermore be used as a mixture with other known herbicides, once again finished formulations or tank mixes being possible. A mixture with other known active ingredients, such as fungicides, insecticides, acaracides, nematicides, bird repellents, growth substances, plant nutrients and agents which improve soil structure, is also possible. For certain intended uses, in particular in the postemergence method, it may furthermore be advantageous to include plant-tolerated mineral or vegetable oils (for example the commercial preparation "Oleo Dupont 11E") or ammonium salts, such as, for example, ammonium sulphate or ammonium thiocyanate, as further additives in the formulations.

The novel active ingredient combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomising, dusting or scattering.

The application rates of the active ingredient combinations according to the invention can be varied within a certain range; they depend, inter alia, on the weather and on the soil factors. In general, the application rates are between 0.01 and 10 kg per ha, preferably between 0.05 and 5 kg per ha, particularly preferably between 0.1 and 3.0 kg per ha.

The active ingredient combinations according to the invention can be applied before or after emergence of the plants, that is to say by the preemergence or postemergence method.

The good herbicidal action of the novel active ingredient combinations is evident from the Examples below. While the individual active ingredients have weaknesses in the herbicidal action, the combinations all exhibit a very good action against weeds, over and above a simple summation of actions.

Herbicides have a synergistic effect whenever the herbicidal action of the active ingredient combination is greater than that of the individual active ingredients applied.

The action to be expected for a given combination of two herbicides can be calculated as follows (cf. COLBY, S. R.; "Calculating synergistic and antagonistic responses of herbicide combinations", Weeds 15, pages 20–22, 1967):

If  $X =$  % damage by herbicide A (active ingredient of group 1) at an application rate of p kg/ha and
$Y =$  % damage by herbicide B (active ingredient of group 2) at an application rate of p kg/ha and
$E =$  the expected damage by herbicides A and B at an application rate of p and q kg/ha,
then  $E = X + Y - (X \cdot Y/100)$.

If the actual damage is greater than calculated, the combination is superadditive in its effect, that is to say it exhibits a synergistic effect.

The Examples which follow show that the herbicidal action found for the active ingredient combinations according to the invention in the weeds is greater than the calculated action, that is to say the novel active ingredient combinations have a synergistic effect.

USE EXAMPLES

For the preparation of the active ingredient formulations required for the tests, corresponding amounts of a water-dispersible powder formulation (WP) of the heteroaryloxyacetamide of the formula ( I-1 ) and a commercial formulation of the active ingredient of group 2 are weighed and are diluted with water to the desired concentration; different combinations of the two active ingredients were prepared by mixing.

A 70 % strength WP was used as a METHABENZTHIAZURON formulation (trade name: ®TRIBUNIL, Bayer AG).

50% strength WG (water-dispersible granules) were used as an ISOPROTURON formulation (trade name: ®ARELON, Hoechst AG).

A 70% strength WP was used as a METRIBUZINE formulation (trade name: ®SENCOR, Bayer AG).

The tests were carried out as follows:
A) Preemergence tests/Greenhouse

Seeds of the test plants are sown in standard soil and, after 24 hours, are watered with the active ingredient formulation. The amount of water per unit area is advantageously kept constant. The active ingredient concentration in the formulation plays no role, only the application rate of the active ingredient per unit area is decisive. After the treatment, the test plants are kept in a greenhouse house under controlled conditions (temperature, atmospheric humidity, light) until the evaluation.

After 3 weeks, the degree of damage to the plants is rated in % damage in comparison with the development of untreated control plants.

The figures have the following meaning:

0 = No effect/damage (like untreated control)
100 = Total destruction

Postemergence tests/Greenhouse

Test plants which have reached a height of 5 to 15 cm are sprayed with the active ingredient formulations so that the amounts of active ingredient desired in each case are applied per unit area. The concentration of the spray liquors is chosen so that the amounts of active ingredient desired in each case are applied in 500 l of water per ha. After the treatment, the test plants are kept in a greenhouse under controlled conditions (temperature, atmospheric humidity, light) until the evaluation. After three weeks, the degree of damage to the plants is rated in % damage in comparison with the development of the untreated control plants.

The figures have the following meaning:

0 = No effect/damage (like untreated control)
100 = Total destruction

Active ingredients, application rates and results are shown in the Tables below, the abbreviations used in the Tables having the following meanings:

(I-1) = N-Isopropyl-N-(4-fluorophenyl)-(5-trifluoromethyl-1,3,4-thiadiazol-2-yloxy)-acetamide;
(IPU) = ISOPROTURON;
(MBT) = METHABENZTHIAZURON;
(MBZ) = METRIBUZINE;
Found = Damage or action found (in percent);
Calc. = Damage or action calculated using the above COLBY formula (in percent).

TABLE A-1

Preemergence test/Greenhouse

| Active ingredient or active ingredient combination | Application rate g/ha (Active ingredient) | Test plants Damage or action in % | | | |
|---|---|---|---|---|---|
| | | Wheat | | Galium | |
| | | Found | Calc. | Found | Calc. |
| (I-1) Known | 125 | 10 | | 70 | |
| (MBT) Known | 1,500 | 0 | | 20 | |
| (I-1) + (MBT) According to the invention | 125 + 1,500 | 10 | 10 | 95 | 76 |

TABLE A-2

Preemergence test/Greenhouse

| Active ingredient or active ingredient combination | Application rate g/ha (Active ingredient) | Test plants Damage or action in % | | | |
|---|---|---|---|---|---|
| | | Wheat | | Alopecurus | |
| | | Found | Calc. | Found | Calc. |
| (I-1) Known | 125 | 10 | | 90 | |
| (MBT) Known | 750 | 0 | | 20 | |
| Known | 1,500 | 0 | | 70 | |
| (I-1) + (MBT) | 125 + 750 | 10 | 10 | 100 | 92 |
| According to the invention | 125 + 1,500 | 10 | 10 | 100 | 97 |

TABLE A-3

Preemergence test/Greenhouse

| Active ingredient or active ingredient combination | Application rate g/ha (Active ingredient) | Test plants Damage or action in % | | | |
|---|---|---|---|---|---|
| | | Wheat | | Lolium | |
| | | Found | Calc. | Found | Calc. |
| (I-1) Known | 125 | 10 | | 60 | |
| (MBT) Known | 1,500 | 0 | | 40 | |
| (I-1) + (MBT) According to the invention | 125 + 1,500 | 10 | 10 | 90 | 76 |

TABLE B-1

Postemergence test/Greenhouse

| Active ingredient or active ingredient combination | Application rate g/ha (Active ingredient) | Test plants Damage or action in % | | | |
|---|---|---|---|---|---|
| | | Barley | | Matricaria | |
| | | Found | Calc. | Found | Calc. |
| (I-1) Known | 125 | 30 | | 50 | |
| (MBT) Known | 125 | 0 | | 80 | |
| (I-1) + (MBT) According to the invention | 125 + 125 | 0 | 30 | 100 | 90 |

TABLE B-2

Postemergence test/Greenhouse

| Active ingredient or active ingredient combination | Application rate g/ha (Active ingredient) | Test plants Damage or action in % | | | |
|---|---|---|---|---|---|
| | | Wheat | | Avena | |
| | | Found | Calc. | Found | Calc. |
| (I-1) Known | 125 | 0 | | 50 | |
| (MBT) Known | 500 | 0 | | 10 | |
| Known | 1,000 | 0 | | 30 | |
| (I-1) + (MBT) | 125 + 500 | 10 | 0 | 98 | 55 |
| According to the invention | 125 + 1,000 | 10 | 0 | 98 | 65 |

TABLE A-4

Preemergence test/Greenhouse

| Active ingredient or active ingredient combination | Application rate g/ha (Active ingredient) | Test plants Damage or action in % | | | |
|---|---|---|---|---|---|
| | | Wheat | | Galium | |
| | | Found | Calc. | Found | Calc. |
| (I-1) Known | 125 | 10 | | 70 | |
| (IPU) Known | 500 | 0 | | 0 | |
| | 1,000 | 10 | | 0 | |
| | 2,000 | 10 | | 20 | |
| (I-1) + (IPU) According to the invention | 125 + 500 | 0 | 10 | 80 | 70 |
| | 125 + 1,000 | 0 | 19 | 90 | 70 |
| | 125 + 2,000 | 10 | 19 | 90 | 76 |

TABLE B-3

Postemergence test/Greenhouse

| Active ingredient or active ingredient combination | Application rate g/ha (Active ingredient) | Test plants Damage or action in % | | | |
|---|---|---|---|---|---|
| | | Barley | | Sinapis | |
| | | Found | Calc. | Found | Calc. |
| (I-1) Known | 125 | 30 | | 40 | |
| (IPU) Known | 125 | 0 | | 70 | |
| (I-1) + (IPU) According to the invention | 125 + 125 | 0 | 30 | 100 | 82 |

TABLE B-4

Postemergence test/Greenhouse

| Active ingredient or active ingredient combination | Application rate g/ha (Active ingredient) | Test plants Damage or action in % | | | |
|---|---|---|---|---|---|
| | | Wheat | | Avena | |
| | | Found | Calc. | Found | Calc. |
| (I-1) Known | 125 | 0 | | 50 | |
| (MBZ) Known | 30 | 0 | | 20 | |
| (I-1) + (MBZ) According to the invention | 125 + 30 | 10 | 0 | 90 | 60 |

TABLE B-5

Postemergence test/Greenhouse

| Active ingredient or active ingredient combination | Application rate g/ha (Active ingredient) | Test plants Damage or action in % | | | |
|---|---|---|---|---|---|
| | | Maize | | Abutilon | |
| | | Found | Calc. | Found | Calc. |
| (I-1) Known | 250 | 0 | | 0 | |
| | 500 | 0 | | 10 | |
| (MBZ) Known | 30 | 0 | | 30 | |
| (I-1) + (MBZ) | 250 + 30 | 0 | 0 | 100 | 30 |
| According to the invention | 500 + 30 | 0 | 0 | 100 | 37 |

TABLE B-6

Postemergence test/Greenhouse

| Active ingredient or active ingredient combination | Application rate g/ha (Active ingredient) | Test plants Damage or action in % | | | |
|---|---|---|---|---|---|
| | | Maize | | Chenopodium | |
| | | Found | Calc. | Found | Calc. |
| (I-1) Known | 250 | 0 | | 30 | |
| | 500 | 0 | | 30 | |
| (MBZ) Known | 30 | 0 | | 30 | |
| (I-1) + (MBZ) According to the invention | 250 + 30 | 0 | 0 | 100 | 51 |
| | 500 + 30 | 0 | 0 | 100 | 51 |

TABLE B-7

Postemergence test/Greenhouse

| Active ingredient or active ingredient combination | Application rate g/ha (Active ingredient) | Test plants Damage or action in % | | | |
|---|---|---|---|---|---|
| | | Maize | | Solanum | |
| | | Found | Calc. | Found | Calc. |
| (I-1) Known | 250 | 0 | | 10 | |
| | 500 | 0 | | 20 | |
| (MBZ) Known | 60 | 0 | | 60 | |
| (I-1) + (MBZ) According to the invention | 250 + 60 | 10 | 0 | 100 | 64 |
| | 500 + 60 | 10 | 0 | 100 | 68 |

TABLE B-8

Postemergence test/Greenhouse

| Active ingredient or active ingredient combination | Application rate g/ha (Active ingredient) | Test plants Damage or action in % | | | |
|---|---|---|---|---|---|
| | | Maize | | Setaria | |
| | | Found | Calc. | Found | Calc. |
| (I-1) Known | 250 | 0 | | 60 | |
| (MBZ) Known | 60 | 0 | | 40 | |
| (I-1) + (MBZ) According to the invention | 250 + 60 | 0 | 0 | 100 | 76 |

TABLE B-9

| Active ingredient or active ingredient combination | Application rate g/ha (Active ingredient) | Postemergence test/Greenhouse Test plants Damage or action in % | | | |
|---|---|---|---|---|---|
| | | Maize | | Digitaria | |
| | | Found | Calc. | Found | Calc. |
| (I-1) | 125 | 10 | | 80 | |
| Known (MBZ) | 250 | 10 | | 80 | |
| Known | 30 | 10 | | 20 | |
| (I-1) + (MBZ) | 125 + 30 | 0 | 19 | 100 | 84 |
| According to the invention | 250 + 30 | 10 | 19 | 100 | 84 |

We claim:

1. A herbicidal composition comprising (1) N-isopropyl-N-(4-fluorophenyl)-5-trifluoromethyl-1,3,4-thiadiazol-2-yl oxy)-acetamide and (2) a synergistically effective amount of metribuzine.

2. A composition according to claim 1, wherein the ratio of (1):(2) is from 1:0.01 to 1:100.

3. A composition according to claim 1, wherein the ratio of (1):(2) is from 1:0.1 to 1:30.

4. A composition according to claim 1, wherein the ratio of (1):(2) is 125:30.

5. A composition according to claim 1, wherein the ratio of (1):(2) is 250:30.

6. A composition according to claim 1, wherein the ratio of (1):(2) is 500:30.

7. A method of combating weeds in the growing of a crop which comprises applying to such weeds, to the crop or to the soil in which said crop is growing or to be grown a selectively herbicidally effective amount of a composition according to claim 1.

8. The method according to claim 7, wherein such crop is soybeans.

9. The method according to claim 7, wherein such crop is corn.

10. The method according to claim 9, wherein the ratio of (1):(2) is 1:0.1 to 1:30.

* * * * *